United States Patent [19]
Wenzel et al.

[11] Patent Number: 5,840,335
[45] Date of Patent: Nov. 24, 1998

[54] SYSTEM FOR THE CONTROLLED RELEASE OF ACTIVE AGENTS AND A PROCESS FOR ITS PREPARATION

[75] Inventors: Udo Wenzel, Halle/Saale; Jurgen Metzner, Halle/Salle; Thomas Rosin, Halle/Neustadt, all of German Dem. Rep.; Halvor Jaeger, Neu-Ulm/Gerlenhofen; Zoser B. Salama, Senden/Wullenstetten, both of Germany

[73] Assignee: Prof. Dr. Udo Wenzel, Halle/Saale, Germany

[21] Appl. No.: 409,941

[22] Filed: Mar. 23, 1995

Related U.S. Application Data

[63] Continuation of Ser. No. 892,727, May 28, 1992, abandoned, which is a continuation of Ser. No. 472,927, Jan. 31, 1990, abandoned.

[30] Foreign Application Priority Data

Jan. 31, 1989 [DD] German Dem. Rep. .. WP A 61 K/325 354-3

[51] Int. Cl.⁶ ............................................. A61K 9/24
[52] U.S. Cl. ................. 424/473; 424/468; 604/890.1; 604/892.1
[58] Field of Search ................... 424/473, 468; 604/890.1, 892.1

[56] References Cited

U.S. PATENT DOCUMENTS

| | | | |
|---|---|---|---|
| 3,845,770 | 11/1974 | Theeuwes et al. | 424/427 |
| 3,916,899 | 11/1975 | Theeuwes et al. | 424/424 |
| 4,016,880 | 4/1977 | Theeuwes et al. | 424/473 |
| 4,036,227 | 7/1977 | Zaffaroni et al. | 424/448 |
| 4,200,098 | 4/1980 | Ayer et al. | 424/424 |
| 4,326,525 | 4/1982 | Swanson et al. | 424/443 |
| 4,612,008 | 9/1986 | Wong et al. | 604/892.1 |
| 4,615,698 | 10/1986 | Guittard et al. | 604/892.1 |
| 4,618,487 | 10/1986 | DuBois et al. | 424/467 |
| 4,624,847 | 11/1986 | Ayer et al. | 424/467 |
| 4,627,850 | 12/1986 | Deters et al. | 604/892.1 |
| 4,662,880 | 5/1987 | Hamel et al. | 424/467 |
| 4,693,886 | 9/1987 | Ayer et al. | 424/467 |
| 4,747,847 | 5/1988 | Magruder et al. | 604/892.1 |
| 4,765,989 | 8/1988 | Wong et al. | 424/473 |
| 4,783,337 | 11/1988 | Wong et al. | 424/468 |
| 4,784,858 | 11/1988 | Ventouras | 424/468 |
| 4,857,330 | 8/1989 | Stephens et al. | 424/424 |
| 4,992,278 | 2/1991 | Khanna | 424/473 |

FOREIGN PATENT DOCUMENTS

| | | |
|---|---|---|
| 52917 | 6/1982 | European Pat. Off. . |
| 0169105 | 1/1986 | European Pat. Off. . |
| 0238189 | 9/1987 | European Pat. Off. . |
| 0277092 | 3/1988 | European Pat. Off. . |
| 0279976 | 8/1988 | European Pat. Off. . |
| 0309051 | 9/1988 | European Pat. Off. . |
| 250374 | 2/1991 | European Pat. Off. . |
| 3400496 | 7/1985 | Germany . |
| 2150434 | 7/1985 | United Kingdom . |

OTHER PUBLICATIONS

The Controlled Porosity Osmotic Pump, Gaylen M. Zentner, et al, Journal of Controlled Release, 1 (1985) pp. 269–282.

*Primary Examiner*—D. Gbrielle Phelan
*Attorney, Agent, or Firm*—Sughrue, Mion, Zinn, Macpeak & Seas, PLLC

[57] ABSTRACT

A system for the controlled release of an active agent to an environment of use, said system having a predetermined release rate of the active agent to the environment of use, comprising: a) a shell comprised of a wall formed of a water-insoluble material which is permeable to the passage of an external fluid, and b) a core which is surrounded by said shell, said core comprised of i) a water-soluble active agent, and ii) a soluble polymeric adjuvant capable of unlimited swelling.

20 Claims, 3 Drawing Sheets

SYSTEM FOR THE CONTROLLED RELEASE OF ACTIVE AGENTS AND A PROCESS FOR ITS PREPARATION

This is a continuation of application Ser. No. 07/892,727, filed May 28, 1992, now abandoned which is a continuation application of application Ser. No. 07/472/927, filed Jan. 31, 1990 now abandoned.

BACKGROUND OF THE INVENTION

1. Field of the Invention

The present invention relates to a system for the controlled release of an active agent and a process for its preparation. The system is also suitable for various kinds of active agents and will be explained in the following using a preferred embodiment, i.e., the release of a pharmaceutical agent, as an example.

The system is preferably used for orally administrable pharmaceutical preparations, especially those that are soluble, operating with essentially even, controlled pharmaceutical agent release which is effected by convective processes.

2. Description of the Prior Art

As regards its therapeutic effectivity, the ideal oral delayed release pharmaceutical preparation must be similar in effectivity to an intravenous drip. In other words, due to the even and complete release of the active agent from the pharmaceutical preparation for a physiologically and therapeutically practical period of time a constant, therapeutic blood level is obtained. This level guarantees the long-term effect of the drug while reducing the adverse effects and improving the local tolerance in the gastrointestinal tract at the same time.

Pharmaceutical preparations in which the active agent release is controlled, i.e., it is independent of marginal conditions, are considered especially advantageous. This is because in such pharmaceutical preparations the constant active agent release is ensured with a high measure of certainty and the in vitro and in vivo release rates are compatible.

It is common knowledge that the release of active agents can be controlled by embedding processes and/or matrix processes, covering or coating processes as well as by osmotically driven systems.

Matrix processes as described, for example, in DD-A-232 821, have the drawback that they usually cannot be used to obtain pharmaceutical agent release according to zero-order kinetics. The literature on release systems on a matrix basis is extensive See, for example, S. D. Bruck, *Controlled Drug Delivery*, Vol. I and II, CRC-Press (1983).

As regards covered pharmaceutical preparations, it is necessary to find a suitable shell that will control the diffusion of the dissolved pharmaceutical agent according to the physico-chemical properties of the active agent. Today, it is almost always polyacrylic acid esters-co-methacrylic acid esters that are used for this purpose.

While it is easier and more accurate to realize the pharmacokinetically favorable release of the zero-order using covered pharmaceutical preparations, they have the enormous drawback that any damage to the shell results in the entire dose incorporated in the pharmaceutical preparation being released within a short period of time (dose dumping). This, in turn, causes significant adverse effects in the patient and jeopardizes therapy safety.

In an attempt to increase the safety level of the conventional single unit delayed release preparation, the total dose was split up into several smaller particles, each of which provide delayed release doses (multiple unit dosage forms), under acceptance of the extreme increase in technological expenditure (S. D. Bruck, *Controlled Drug Delivery*, Vol. I and II, CRC-Press (1983); R. Baker, *Controlled Release of Bioactive Material*, Acad. Press (1980); Y. W. Chien, *Novel Drug Delivery Systems*, Marcel Dekker (1982); J. R. Robinson, *Sustained and Controlled Release Drug Delivery Systems*, Marcel Dekker (1978)).

The osmotically driven systems described, for instance, by Theeuws in *J. Pharm. Sc.*, Vol. 64, 12, pages 1987 to 1991 or in DE-A-26 40 193 and EP-A0 169 105 exhibit an almost ideal release rate which is independent of marginal conditions and permits the maintenance of the desired serum level for a therapeutically and physiologically practical period of time.

In principle, osmotic systems have one or more release openings whose preparation (e.g., by means of laser drills) usually entails high technological costs. An exact description of the preparation of the release openings and their minimum and maximum dimensions can be found in US-A-3,845,770 and in 3,916,899.

The serious side effects which occurred in medication with osmotic systems and led to the withdrawal of these osmotically releasing pharmaceutical preparations for Indomethacin (see Martin, A. N., *Physikalische Pharmazie*, Ed. H. Stricker, 3rd Edition, page 576, Stuttgart 1987) were said to be caused by the concentrated release of the pharmaceutical agent from the release opening or openings (the so-called flame-cutter effect).

Thus, there is a need for the provision of a system for the controlled release of active agents and a process for its preparation, preferably for high soluble and easily soluble pharmaceutical agents.

SUMMARY OF THE INVENTION

An object of the present invention is to provide a system for the controlled release of an active agent in which, in the case of a pharmaceutical agent, the release of the active agent occurs throughout a physiologically and therapeutically practical period of time, preferably under zero-order kinetics and, as far as possible, is independent of the marginal conditions.

A further object of the present invention is to provide a system in which the lag time commonly characteristic of osmotically releasing systems can be selectively adjustable.

Another object of the present invention is to provide a system in which the release pattern is to remain unchanged, at least essentially, even if the controlling membrane that controls the release rate is damaged.

Still another object of the present invention is to provide a system in which release is preferably to occur over the entire surface of the pharmaceutical preparation in order to prevent the possibility of damage caused by the release of highly concentrated pharmaceutical preparation-adjuvant solutions at one site.

Yet another object of the present invention is to provide a system in which the delayed release of the active agent is brought about by use of suitable adjuvants that are industrially available, pharmaceutically and technologically easy to process and non-toxic.

A further object of the present invention is to provide a system which can employ a wide variety of active agents, such as plant protectives, fertilizers or growth regulators.

Additional objects and advantages of the present invention will be set forth in part in the description which follows and in part will be obvious from the description or can be learned by practice of the invention. The objects and advantages are achieved by means of the processes, instrumentalities and combinations particularly pointed out in the appended claims.

To achieve the foregoing objects and in accordance with its purpose, the present invention provides a system for the controlled release of an active agent to an environment of use, the system having a predetermined release rate of the active agent to the environment of use, comprising:

a) a shell comprised of a wall formed of a water-insoluble material which is permeable to the passage of an external fluid, b) a core which is surrounded by said shell, and comprised of
  (i) a water-soluble active agent, and
  (ii) a soluble polymeric adjuvant capable of unlimited swelling and having a less pronounced tendency to hydrate than the active agent, said active agent and said polymeric adjuvant being hydrated when the external fluid permeates through the shell, said active agent being present in an amount which provides a saturated solution of active agent in the core at said predetermined release rate, to thereby provide a predetermined solved amount of said active agent at said predetermined release rate, said polymeric adjuvant being present in an amount which provides a saturated solution of said polymeric adjuvant at said predetermined release rate to thereby provide a predetermined solved amount of polymeric adjuvant at said predetermined release rate, and said predetermined solved amounts of active agent and polymeric adjuvant creating a predetermined hydrostatic pressure,
  (iii) wherein the active agent and polymeric adjuvant are present in a ratio such that
  (iv) in case the release rate of the active agent deviates from the predetermined release rate by being higher than the predetermined release rate, an additional amount of polymeric adjuvant becomes solved and is delivered to the shell where it acts to decrease the permeability of the shell and thereby decrease the deviation
  (v) in case the release rate of the active agent deviates from the predetermined release rate by being lower than the predetermined release rate, an additional amount of active agent becomes solved to increase the hydrostatic pressure above said predetermined hydrostatic pressure, said increased hydrostatic pressure acting on said shell to increase the permeability of the shell and thereby decrease the deviation.

In one embodiment of the present invention, the shell is comprised of a material which is substantially impermeable to the passage of the active agents, and thus is a semipermeable material, and is provided with a passageway for dispensing said agent from the system.

In a second embodiment of the invention, the shell is comprised of a material which is permeable to the passage of the active agent.

In a third embodiment of the present invention, the shell is comprised of a material which is substantially impermeable to the passage of the active agent, and is not provided with any passageways through the shell.

In one aspect of the invention, there is provided a system for the controlled release of an active agent comprising (a) a core containing at least one water-soluble active agent, at least one osmotically active substance and at least one polymeric adjuvant capable of unlimited swelling, which polymeric adjuvant has a less pronounced tendency to hydrate than the active agent and osmotically active agent, and comprising a semipermeable shell made of a film former and a soluble, hydrophilic or hydrophobic plasticizer.

In another aspect of the present invention, there is provided a process for the preparation of a system for the controlled release of an active agents comprising, mixing at least one water-soluble active agent with at least one osmotically active adjuvant and at least one polymeric adjuvant capable of unlimited swelling, the polymeric adjuvant capable of unlimited swelling having a less pronounced tendency to hydrate than the active agent and osmotically active adjuvant, compressing the mixtures into a core, and then covering the core with a shell made of a film former and a soluble, hydrophilic or hydrophobic plasticizer.

It is to be understood that both the foregoing general description and the following detailed description are exemplary and explanatory, but are not restrictive of the invention.

DETAILED DESCRIPTION OF THE INVENTION

Figure 1:
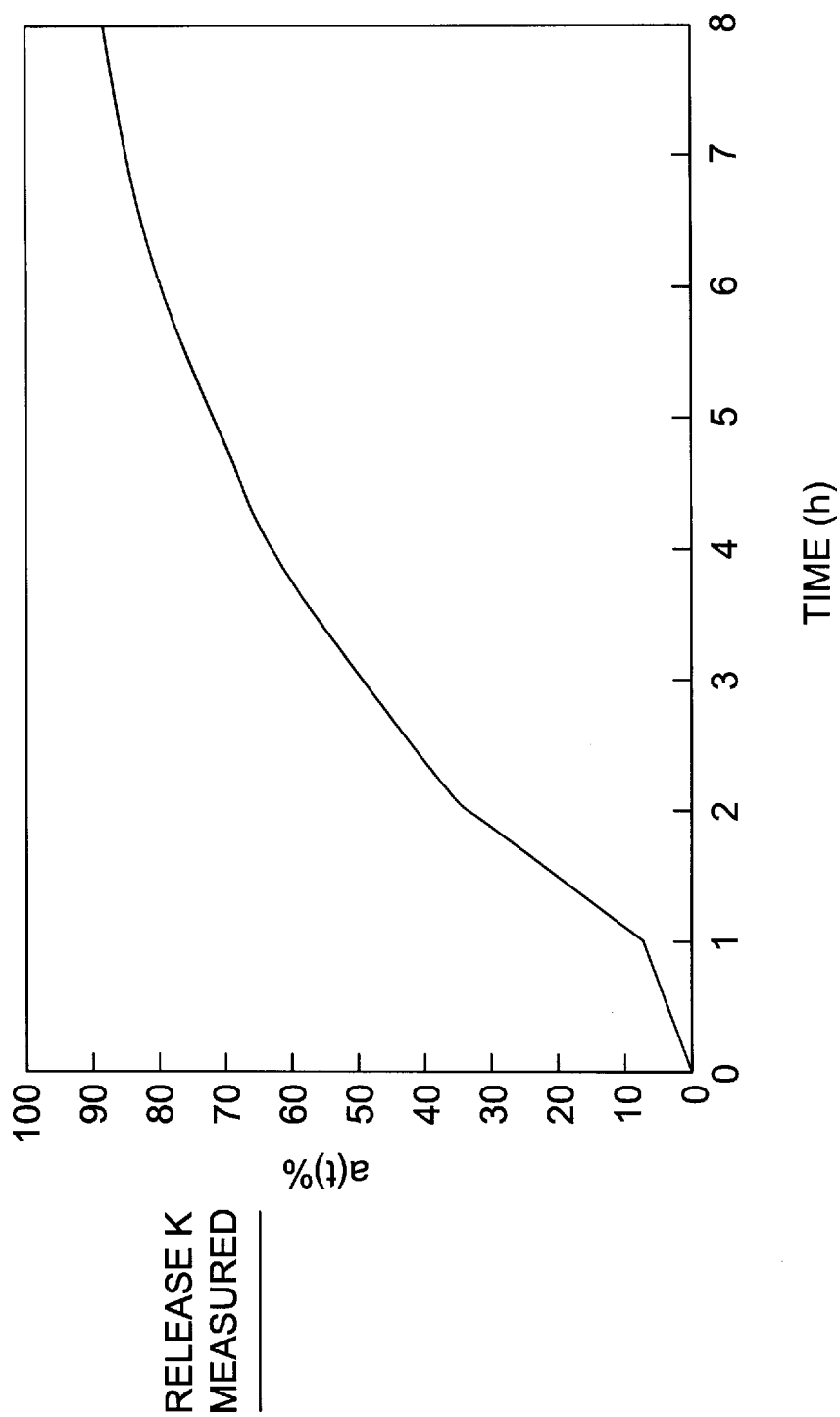
FIG. 1 shows the release of diltiazem from pharmaceutical preparations according to Example 2 ("Release K")

Osmosis is the passage of a solvent through a semipermeable membrane separating two solutions of different concentration of a substance. Solvent passes through the membrane in the direction of the higher concentrated solution. Osmosis will stop when the two solutions reach equal concentration and/or will stop by applying a pressure to the side with higher concentration.

Osmotic pressure depends only on the number of particles in solution and is independent from the (kind) nature of the particles. Thus, the osmotic pressure is governed by the sum of all solved particles, regardless of their kind.

Well known osmotic systems act and are constructed in such a manner that the release rate of active agent from the system is determined by (a) the osmotic activity and osmotic gradient between the system and environment, determined by the core composition, and (b) the permeability of the system determined by the area of the release openings of semipermeable membrane.

Osmotic systems act with a defined hydrostatic pressure in the core, which pressure depends on the osmotic activity of the core material and the area of the release openings in the shell. The amount of active agent that is released is a function of the hydrostatic pressure in the core and the area of the release openings in the shell.

If the area of the release openings is changed, there will be a change in the released amount of active agent. If the area of the release openings is increased, the system will provide a larger release rate than its predetermined release. If the area of the release openings is decreased, the system will provide a smaller release rate than its predetermined release rate. In the past, changes in the membrane and in the area of the release openings generally are irreversible and result in irreversible changes in the release rate of active agent.

If the area of the release openings is decreased, such as can occur by the shell becoming bound to the lining of the stomach or by food and other particles clogging the release openings, there will be an increase in the hydrostatic pressure in the system with the danger that the shell will rupture. If the membrane is able to resist the higher hydrostatic pressure, there will be a decrease in the amount of active agent which is released as a result of the decreased permeability of the shell.

If the area of the release openings is increased, such as can occur by the shell becoming accidentally damaged during storage or prior to use, there will be a decrease in the hydrostatic pressure in the system, an increase in the permeability of the shell and an increase in the amount of active agent which is released as a result of the increase in permeability of the shell.

The continuous controlled release system of the present invention provides, by using a specific composition of the core and shell, a regulation mechanism for a) controlling the osmotic activity of the core and b) controlling the permeability of the shell during the lifetime of the system. The system of the present invention is controlled by its regulation mechanism in a manner such that the system is able to return to its predetermined release rate.

During the solvation process of a water-soluble substance, the substance becomes solved by coming into contact with water, and there is a release of free enthalpy to the environment, which release is characteristic for the particular substance which :Ls being solved. Thus, different types of molecules release different amounts of free enthalpy during solvation. For each molecule that is solvated there is a release of free enthalpy to the environment. The free enthalpies released during solvation differ per mole of different substance. The free enthalpy release of a readily soluble substance is greater than the free enthalpy release of a less soluble substance. In the present invention, the active agent is more soluble than the polymeric adjuvant and thus releases more free enthalpy during solvation of an equal amount of molecules than the polymeric adjuvant which has a less pronounced tendency to hydrate than the active agent.

In the present invention, the number of water molecules needed or bound during solvation of a single molecule of the active agent is less than the number of water molecules needed or bound during salvation to a single molecule of polymeric adjuvant because the polymeric adjuvant has more binding sites.

In an ideal system (strongly diluted system), there are no interactions between two different substances during their solvation, that is, each substance becomes solvated independently of the solvation of the remaining substance. This occurs in an ideal system because there is an unlimited access to water, and each substance does not have to compete with the remaining substance for the water molecules.

A real system, that is, a system in which there is a limited amount of water, differs from the ideal system because there are interactions between the solved molecules of different substances. As a result of this interaction, the amount of solved molecules of a first substance depends on the amount of molecules of a second substance that is available for salvation.

In a static, closed system comprised of a saturated solution containing a saturated amount of active agent and a saturated amount of polymeric adjuvant, there are not enough water molecules to solve all the molecules of either or both substances. In such a saturated solution, there will be a defined ratio (K) between the number of solved molecules of active agent and the number of solved molecules of polymeric adjuvant. Thus, in such a saturated solution, there is a predetermined solved amount of active agent and a predetermined solved amount of polymeric adjuvant. These predetermined amounts are governed by the relative ability of each substance to become solved, with the substance having the higher ability to become solved being present in a higher solved amount than the substance having lesser ability to become solved.

If the system of the present invention comes into contact with the external fluid of the environment, water is imbibed into the core and provides a hydrostatic pressure. Theoretically, the passage of water through the permeable membrane will cease when the hydrostatic pressure which acts against the passage of water molecules through the shell into the core reaches the osmotic pressure, which osmotic pressure is predetermined by the core material.

The increasing hydrostatic pressure leads, at least at a certain point, to the outflow of solute, that is, dissolved active agent and dissolved polymeric adjuvant. The released amount of solved dissolved agent and dissolved polymer adjuvant will be a function of the saturation ratio (k) and will be stabilized with the lowest free enthalpy at the flow through conditions. Each change in flow through the system changes the thermodynamic energy content of the system.

At a given point of available water in the system, there is a given ratio of the number of solved particles of active agent and solved particles of polymeric adjuvant. The sum of the number of particles determines the osmotic pressure at this given point. (This osmotic pressure governs the hydrostatic pressure which governs the release rate (outflow) of the solved particles of active agent and solved particles of polymeric adjuvant. This hydrostatic pressure, as discussed above, also acts against the inflow of water). At some point in time, the inflow and outflow will become equal, and there will be a steady state release of solved particles of active agent and solved particles of polymeric adjuvant.

At any given point in the predetermined release rate of the system, if the inflow of water decreases from the predetermined inflow, the outflow of solute (and release rate) also will decrease, and the ratio between the numbers of solved particles of active agent to polymeric adjuvant in the core will increase. (The system is driven to the stable and static end point). With a given number of water molecules in the given volume of the core at a given point of time, some of the molecules of the polymeric adjuvant will be dehydrated. Since each particle of polymeric adjuvant binds more water than a particle of active agent, dehydration of the polymeric adjuvant will lead to an increase in the number of solved particles of active agent greater than the number of particles of polymeric adjuvant which were dehydrated. Since the total number of particles in the system therefore will be greater, there is an increase in the osmotic pressure. The osmotic gradient between core and environment therefore will increase, and this will result in an increase in the inflow of water into the core through the membrane, which, in turn, will. result in an increase in the hydrostatic pressure. The increase in hydrostatic pressure, in turn, will lead to a higher outflow of solute. By this mechanism, the release rate will normalize and return to the predetermined release rate at this point in the lifetime of the system.

The increase in hydrostatic pressure also acts to increase the pore size of existing pores and if the increase is great enough to form new pores. The resulting increased permeability thus also acts to return the system to its predetermined release rate.

Further, as a result of the dehydration of the polymeric adjuvant, the viscosity will decrease because the solved molecules of the polymeric adjuvant are larger than the solved molecules of active agent. As a result of the decrease in viscosity, there will be a greater outflow of water than before, and thus this phenomena also acts to return the system to its predetermined release rate.

At any given point in the predetermined release rate of the system, if the inflow of water increases from the predetermined inflow, the outflow of solute and the release rate also will increase, and the ratio of the number of solved particles of active agent to polymeric agent in the core will decrease. (The system is driven to a more diluted system). By a given number of water molecules in the given volume of the core at a given point in time, some of the molecules of the polymeric adjuvant will be solved. Since each particle of polymeric adjuvant binds more water than a particle of active agent, solvation of the polymeric adjuvant will lead to a decrease in the number of solved particles of active agent greater than the number of particles of polymeric adjuvant which were solved. Since the total number of particles in the system therefore will be less, there is a decrease in the osmotic pressure. The osmotic gradient between core and environment therefore will decrease, and this will result in a decrease in the inflow of water into the core through the shell, which, in turn, will result in a decrease in the hydrostatic pressure. The decrease in hydrostatic pressure, in turn, will lead to a decreased outflow of solute. By this mechanism, the release rate will normalize and return to the predetermined release rate at this point in the lifetime of the system.

Further, as a result of the increased amount of polymeric adjuvant that becomes solved, additional solved polymeric particles will be available in the system and will be transported toward the shell where, because of their larger size, they will tend to block the openings and become part of the shell, thereby reducing the size of the openings. This reduction in size of the openings thus also acts to decrease the permeability and flow rate and thus also acts to return the system to its predetermined release rate.

Further, as a result of the solvation of the polymeric adjuvant, the viscosity will increase because the solved molecules of the polymeric adjuvant are larger than the solved molecules of the active agent. As a result of the increase in viscosity, there will be a lesser outflow of water than before, and thus this phenomena also acts to return the system to its predetermined release rate.

As regards solubility, a high solubility substance is one to which less than 30 parts by weight of solvent have to be added. to dissolve 1 part by weight thereof. See, *Arzneibuch der DDR*, Akademie Verlag, Berlin 1985, I/II/4.0.

In the system of the present invention, the release of the active agents is controlled by forming a core containing the active agent and the polymeric adjuvant which has a relatively low osmotic activity, and then covering the obtained core with a suitable wall material, the compatibility of the properties of the wall and core materials being such that in a lag phase, water flows through the wall material (membrane) which has solute (salt-retaining) properties, the water flow being determined by the osmotic activity of the core material.

The system of the invention can be produced with at least: one release opening or passageway in the shell (membrane), prepared in the usual manner, to provide a semipermeable membrane for the active agent solution. The area of the passageway can be determined and the manufacture of the passageway can be in accordance with the descriptions in U.S. Pat. No. 3,916,899 which is hereby incorporated by reference in its entirety.

If no such opening has been prepared, the shell as produced is permeable to water but impermeable to active agent. Then, during use of the system, the hydrostatic pressure that builds up during the lag phase will selectively loosen up the wall structure and induce the formation of micropores (pore size in the $\mu m$ range). This, in turn, will lead to the active agent solution being pumped out by means of essentially convective processes. The hydrostatic pressure is the cause of the active agent release.

A self-regulation will occur and eventually a steady state constant release rate can be achieved.

In still another embodiment of the invention, the system can be manufactured with a shell that is permeable to both fluid and active agent. In this embodiment of the invention, when fluid enters the core, the amount of water available for solving the active agent and polymeric adjuvant is unlimited. As a result, there will be available a relatively large amount of solved polymeric adjuvant particles which can be transported to the shell where they act to decrease the permeability of the shell, resulting in a reduced inflow of water and a reduced release rate. A self-regulation will occur and eventually a steady state constant release can be achieved.

In the present invention, a water-soluble active agent is employed. The term "active agent" as used herein refers to an agent which can be delivered from the system to produce a beneficial result. The active agent must be soluble in the fluid that enters the core and functions as an osmotically active solute. If the active agent has a relatively low solubility in the fluid and thus a relatively low osmotic activity, it can be mixed with an osmotically active adjuvant that is soluble in the fluid that enters the core. The active agent, and when present, the combination of active agent and osmotically active adjuvant, determines the osmotic activity of the core. The amount of active agent or active agent admixed with other osmotically active adjuvants present in the core are in excess of the amount that can be dissolved in the fluid that enters the core, and under this physical state when the active agent or active agent and osmotically active adjuvant are in excess, the system can osmotically operate to provide a substantially constant rate of release and can operate in accordance with the self-regulating control mechanism of the present invention.

Examples of suitable osmotically active adjuvants with enough osmotic activity are lactose, fructose, dextrose, sucrose, mannitol, sodium chloride, potassium chloride, potassium sulphate and mono-, di and trisodium phosphate and mixtures thereof.

The osmotically active adjuvant can be a substance with buffer activity. If the active agent is osmotically active enough itself, it can take over the function of the osmotically active adjuvant. In that case, there is no requirement for an additional osmotically active adjuvant.

In the system of the present invention, the active agent, or the combination of active agent and osmotically active adjuvant, are employed in a concentration of 2 to 98 weight percent, based on the total weight of the core.

In the system of the present invention, there is present in the core, as an essential component, a polymer adjuvant capable of unlimited swelling. Substances which swell can be of two types, those of unlimited swelling ability and those of limited swelling ability. Substances of unlimited swelling ability are characterized in that the forces which cause the increase in volume result from the solvent interacting with macromolecules and are stronger than the binding/cohesion forces of the molecule/molecule aggregate. If enough solvating agent is present, the substance capable of unlimited swelling will dissolve, thus causing the intermediate formation of a more or less pronounced gel phase. Substances of limited swelling ability are characterized in that the forces which cause the increase in volume result from the sorption/binding of water and are not stronger than the binding/cohesion forces in the molecule or molecule aggregate, and thus the increase in volume stops.

Examples of suitable polymeric adjuvants capable of unlimited swelling which can be used in the present invention are polyvinyl alcohols, preferably with a residual acetate content of 6 to 18% and an average molecular weight of 20,000 to 70,000, and cellulose compounds such as methyl cellulose, methylethyl cellulose, hydroxypropyl cellulose, hydroxypropylmethyl cellulose and carboxymethyl cellulose. These polymeric adjuvants capable of unlimited swelling exhibit a less pronounced tendency to hydrate than the employed active agent or combinations of the employed active agents with the osmotically active adjuvants. If the polymeric adjuvants are suitable, they will precipitate in a saturated aqueous solution of the osmotically active adjuvant and/or active agent. It is also possible to use other conventional pelleting adjuvants such as suitable binder, fillers and lubricants.

In the system of the invention, the polymeric adjuvant capable of unlimited swelling can be used in a concentration of 5 to 90, preferably 5 to 60, weight percent, based on the total weight of the core. A lower amount such as 2 weight percent can be used under appropriate conditions.

The shell is comprised of a suitable water-permeable film former, known per se, such as cellulose acetate, ethyl cellulose, polyvinyl acetate or a polyacrylic acid copolymers. The film former can be used with a soluble, hydrophilic (e.g. a polyethylene glycol) or hydrophobic (e.g. rinseed oil) plasticizers. A preferable plasticizer is a polyethylene glycol having an average molecular weight of 400 to 20,000. The plasticizer is preferably employed in an amount of 2 to 30 weight percent, based on the weight of the film former.

The film former coating is such that it imparts solute (salt-retaining) properties, which will be referred to as semipermeable properties, to the shell of the system.

If a suitable osmotically active substance with buffer activity is used (e.g. mono- or bi-basic salts of phosphoric acid), a suitable pH environment can be advantageously adjusted in the core of the system in a manner known to those of ordinary skill in the art. This is done to also provide optimum solution conditions and, by making use of convective processes, release conditions for pH-dependent soluble active agents, or to influence in the desired manner the pH-dependent swelling of the hydrophilic, polymeric adjuvant capable of unlimited swelling.

According to the invention, the controlled release of the active agent takes place via at least three different mechanisms: 1. Via the properties of the shell (control membrane) such as thickness, surface, water permeability, pore number and size, all of which can be regulated in a manner known per se, 2. Via the properties of the core material whose composition determines the osmotic pressure and the viscosity of the forming active agent/adjuvant solution, and 3. Via the ratio of the saturation solubility of the soluble active agents and adjuvants in use.

The polymeric adjuvant capable of unlimited swelling which is incorporated into the core material is present, under the usual conditions (intact shell), in a "salted-out" condition —i.e., only slightly hydrated and thus only slightly dissolved.

If the shell is damaged, there is an excess of water which is no longer bound by the osmotically active substance, and this will cause the adjuvant to swell. The adjuvant thus counteracts the uncontrolled inflow of water and the uninhibited outflow of the rapidly dissolving pharmaceutical agent. This, in turn, causes an increase in the concentration of the osmotically active substance with the higher affinity to water, and as a result the adjuvant capable of swelling is at least partially dehydrated at the shell and can return to the solid state at the shell wall.

It was surprising and unforeseeable that the incorporation of hydrophilic, polymeric adjuvants capable of unlimited swelling into the core material of the system according to the invention did not lead to a swelling of the polymer, as it is described in EP-A-0 277 092 where it is used to control the release of low solubility pharmaceutical agents, and that it did not lead to a marked increase in the viscosity of the active agent/adjuvant solution in the compartment produced by the shell prepared according to conventional and known processes. The swelling and marked increase in viscosity would have been expected to become apparent in an essential decrease in the release of the active agent/adjuvant solution through the pores of the semipermeable shell.

In addition to the advantageous effect of the improved tablettability of the core material of the present invention caused by the use of the hydrophilic, polymeric adjuvants which are capable of unlimited swelling and have good binding properties, in the present invention if the shell is intact, the influence of the polymeric adjuvant on the active agent release from the system is negligible. However, in the case of a damaged shell, which will nullify the function, and thus safety, of today's known, conventional membrane controlled/membrane porosity controlled release systems for pharmaceutical agents, it was surprisingly found that the composition according to the invention guaranteed the functionality, and thus safety, of the system. This has clearly detectable advantages as regards the therapeutic safety and the technologically easy and inexpensive preparation of the system according to the invention, too.

It is known to expect the release pattern of the active agent or agents to vary if the layer thickness of the shell is varied when carrying out a conventional procedure. It is also common knowledge that the layer must have a minimum thickness in order to obtain sufficiently long retardation and, in particular, a linearization of the release curve (referred to a release according to zero-order kinetics in this description). It is typical for a lag phase to occur during release which lasts for a more or less long period of time and in which no active agents, or only therapeutically insignificant amounts thereof, are released (K. Heilmann, *Therapeutische Systeme*, Georg Thieme, Stuttgart 1978). The systems and process according to the present invention, such as those containing a pharmaceutical preparation, can achieve the advantageous linearization of the release pattern even in the case of minimal layer thickness.

The system of the invention can be present in the form of conventional formulations such as tablets or capsules (single unit drug dosage forms). It can also be a multi-compartment form, or a part thereof, and, for example, be filled into a capsule. The multicompartment form means dividing the total dose into several small units (microforms such as microcapsules, pellets and microtablets; small microunits, usually having a size of under 3 mm, obtained by various preparation processes, e.g., coacervation, extrusion, compression, tabletting).

Specific examples of the high solubility active agents that are suitable for the release system are pholedrine sulphate and diltiazem. According to the teaching of the present invention, each of these active agents enables the preparation of advantageous controlled release systems if the core components are used according to the teachings of this invention.

In principle, the aforedescribed systems can be used for various active agents. In addition to the active agents used in agricultural chemistry such as fertilizers, plant protectives, e.g. insecticides and growth regulators, they can be used with preference for pharmaceutical agents in the field of human and veterinary medicine. The use thereof is limited by the saturation solubility and the depot dosage of the active agent. In this regard, it is the ratio of the saturation solubilities of the osmotically active compound and the active agent or active agent mixture which is important. This is because it determines the required amount of osmotically active adjuvant and thus the total weight of the system and its administrability. If the active agents have very high solubility, it is also possible to incorporate very large doses. If its solubility is poor, this form of active agent can only be incorporated in relatively small doses. The use of lower solubility osmotically active adjuvants (e.g. potassium sulphate) improves the usability of low solubility active agents.

The following examples are given by way of illustration to further explain the principles of the invention. These examples are merely illustrative and are not to be understood as limiting the scope and underlying principles of the invention in any way. All percentages referred to herein are by weight unless otherwise indicated.

EXAMPLE 1

In this example, the invention is explained in connection with the use of the following components for the core.

Active agent: pholedrine sulphate (which is used for a soluble pharmaceutical agent), Osmotically active compound: potassium chloride (as an example of the numerous possible osmotically active compounds), Soluble polymer: polyvinyl alcohol (PVA) capable of swelling, type 55/12, VEB Chem. Werke Buna, Schkopau, German Democratic Republic as an example of a polymeric adjuvant capable of swelling and having a less pronounced tendency to hydrate than the osmotically active component (s).

The shell is made of Cellulose-2,5-acetate as a film former, and is employed with polyethylene glycol PEG 600 as a hydrophilic plasticizer.

In this example, four different systems are formulated, with each system having the same shell composition, but different core compositions. Each core composition is of the same weight and contains pholedrine sulfate as an active agent and potassium chloride as an osmotically active substance, but the amounts of these two components differ in the different core compositions. Moreover, the first system, identified herein as System 1a, does not contain any polymeric adjuvant, whereas the other three systems identified herein as Systems 1b, 1c and 1d, contain differing amounts of polymeric adjuvant.

Each core is made by compressing the core components, by a conventional technique, to produce a formed body having a diameter of 7 mm. Each core is then covered with the shell composition to form a shell thickness of 60 Am by using a conventional technique. The shell composition is applied to the core from an acetone solution of the shell components. The shell which is produced is a permeable shell, that is, it is permeable to the passage of active agent. The composition of the shell and the compositions of the core are set forth below.

| Shell Composition: | |
|---|---|
| Cellulose-2,5-acetate | 100 parts by weight |
| Polyethylene Glycol 600 | 25 parts by weight |
| Core Composition 1a | |
| Pholedrine Sulfate | 60.0 mg |
| Potassium Chloride | 190.0 mg |
| Total Weight | 250.0 mg |
| Core Composition 1b | |
| Pholedrine Sulfate | 60.0 mg |
| Potassium Chloride | 165.0 mg |
| PVA 55/12 | 25.0 mg |
| Total Weight | 250.0 mg |
| Core Composition 1c | |
| Pholedrine Sulphate | 60.0 mg |
| Potassium Chloride | 152.5 mg |
| PVA 55/12 | 36.5 mg |
| Total Weight | 250.0 mg |
| Core Composition 1d | |
| Pholedrine Sulphate | 60.0 mg |
| Potassium Chloride | 127.5 mg |
| PVA 55/12 | 62.5 mg |
| Total Weight | 250.0 mg |

The release pattern of each of the above pharmaceutical preparations comprised of the shell and core of the above compositions was determined as the released amount of pholedrine sulphate (wt), ± standard deviation (s), in n=6 determinations (according to USP XXI, Paddle Method, release Medium=water) and is set forth below:

| System 1a | | | | | | | | | | | |
|---|---|---|---|---|---|---|---|---|---|---|---|
| t [min] | 0 | 15 | 30 | 60 | 120 | 180 | 240 | 300 | 360 | 420 | 480 |
| wt [mg] | 0 | 0.3 | 0.8 | 3.7 | 30.9 | 45.5 | 52.4 | 55.3 | 56.9 | 57.5 | 58.3 |
| ±s | 0 | 0.2 | 0.5 | 2.3 | 2.8 | 2.0 | 2.3 | 1.0 | 0.5 | 0.3 | 0.1 |

-continued

System 1b

| t [min] | 0 | 15 | 30 | 60 | 120 | 180 | 240 | 300 | 360 | 420 | 480 |
|---|---|---|---|---|---|---|---|---|---|---|---|
| wt [mg] | 0 | 0.5 | 0.9 | 5.3 | 18.2 | 29.2 | 38.6 | 43.9 | 47.4 | 50.1 | 52.0 |
| ±s | 0 | 0 | 0.1 | 1.5 | 3.8 | 1.4 | 0.8 | 0.9 | 1.1 | 0.4 | 0.5 |

System 1c

| t [min] | 0 | 15 | 30 | 60 | 120 | 180 | 240 | 300 | 360 | 420 | 480 |
|---|---|---|---|---|---|---|---|---|---|---|---|
| wt [mg] | 0 | 1.8 | 3.9 | 8.8 | 17.7 | 25.4 | 32.5 | 37.6 | 41.7 | 45.5 | 48.8 |
| ±s | 0 | 0.9 | 0.7 | 0.7 | 0.5 | 1.0 | 2.2 | 1.1 | 0.8 | 0.9 | 0.5 |

System 1d

| t [min] | 0 | 15 | 30 | 60 | 120 | 180 | 240 | 300 | 360 | 420 | 480 |
|---|---|---|---|---|---|---|---|---|---|---|---|
| wt [mg] | 0 | 0.8 | 1.8 | 3.6 | 10.0 | 15.8 | 20.8 | 26.6 | 33.7 | 38.8 | 42.2 |
| ±s | 0 | 0.2 | 1.4 | 1.0 | 1.0 | 0.7 | 1.1 | 2.9 | 0.7 | 1.8 | 0.4 |

In Systems 1a to 1d there was, at first, a low pholedrine sulphate release. In System 1a there was no zero order release over the release period. This is due to the fact that the permeability necessary for the functionality of an osmotically releasing zero order system has not yet been achieved.

However, as shown by Systems 1b, 1c and 1d, the higher the amount of PVA, the greater the linearization of the curves and thus a closer approach to zero order release.

The release pattern of pharmaceutical preparation according to the composition of System 1d of Example 1 as the released amount of pholedrine sulphate (wt), ± standard deviation in n=6 determinations, is shown by the following data where the total release area is expressed as membrane damage. The release data for System 1d which is set forth above is also set forth below for ease of comparison.

System 1d
With no membrane damage:

| t [min] | 0 | 15 | 30 | 60 | 120 | 180 | 240 | 300 | 360 | 420 | 480 |
|---|---|---|---|---|---|---|---|---|---|---|---|
| wt [mg] | 0 | 0.8 | 1.8 | 3.6 | 10.0 | 15.8 | 20.8 | 26.6 | 33.7 | 38.8 | 42.2 |
| ±s | 0 | 0.2 | 1.4 | 1.0 | 1.0 | 0.7 | 1.1 | 2.9 | 0.7 | 1.8 | 0.4 |

System 1d-I
With membrane damage 640 μm:

| t [min] | 0 | 15 | 30 | 60 | 120 | 180 | 240 | 300 | 360 | 420 | 480 |
|---|---|---|---|---|---|---|---|---|---|---|---|
| wt [mg] | 0 | 1.8 | 5.5 | 9.3 | 16.3 | 22.6 | 29.6 | 35.4 | 41.5 | 45.7 | 48.2 |
| ±s | 0 | 1.5 | 2.6 | 1.3 | 2.0 | 1.1 | 1.9 | 1.5 | 0.4 | 0.7 | 0.2 |

System 1d-II
With membrane damage 3000 μm:

| t [min] | 0 | 15 | 30 | 60 | 120 | 180 | 240 | 300 | 360 | 420 | 480 |
|---|---|---|---|---|---|---|---|---|---|---|---|
| wt [mg] | 0 | 2.2 | 7.8 | 13.9 | 22.3 | 29.1 | 36.1 | 41.6 | 46.2 | 49.5 | 51.3 |
| ±s | 0 | 1.3 | 2.3 | 1.1 | 1.4 | 0.9 | 0.3 | 1.3 | 0.8 | 0.9 | 0.4 |

System 1d which contains 25% of polyvinyl alcohol in the core, and thus comes very close to the ideal release profile of zero-order kinetics.

It is, however, surprising that the large amount of cold water-soluble polyvinyl alcohol capable of swelling in System 1d does not cause the thin shell to burst or initiate an extreme decrease in the release rate of the incorporated pharmaceutical agent.

The release pattern of System 1d starting with different initial permeabilities for the shell was determined and is set forth below. The different permeabilities were provided by providing the shell with different total release opening areas, and in some tests the total area of the shell was so large as to correspond to damage to the shell. Thus, additional openings, having a diameter of up to 3000 μm, were prepared in the shell and ordinarily would be expected to have a strong effect on or nullify the functionality of the pharmaceutical agent release system, which is only 7 mm in diameter itself. This expected effect can be proved in control tests using known osmotically releasing systems or pharmaceutical preparations that were not. prepared according to the process of the invention.

The above data shows that after 8 hours, a pharmaceutical agent release System 1d-II according to the present invention and having a shell damage of 3000 μm, provided a total release which was only 8 mg greater than the release provided with a shell having no damage (System 1d).

The following figures are to give even clearer evidence of these circumstances. The initial and mean release rate from pharmaceutical preparations according to Example 1, System 1d, membrane thickness 60 μm, n=6 determination, with different total release opening area, given as membrane damage, is shown below.

| Membrane Damage [μm] | | Initial Release Rate [mg/h] | Mean Release Rate [mg/h] |
|---|---|---|---|
| Without | (1d) | 4.2 ± 4.9 | 6.1 ± 0.2 |
| 230 | | 7.6 ± 4.5 | 6.0 ± 0.3 |
| 640 | (1d-I) | 14.6 ± 9.1 | 6.5 ± 0.7 |
| 1670 | | 19.9 ± 7.1 | 6.8 ± 0.5 |
| 3000 | (1d-II) | 22.4 ± 6.7 | 7.0 ± 0.5 |

In the system according to the invention, even larger-scale damage in the shell will be compensated for, and this enhances the safety of the pharmaceutical agent administration.

It is of further advantage that the active transport of the incorporated active agent(s) out of the pharmaceutical preparation makes the active agent release more complete, and thus the availability of the active agent is higher than in matrix pharmaceutical preparations, for instance.

EXAMPLE 2

The effectiveness of the systems and process according to the invention is underlined by the in vitro and in vivo behavior of the pharmaceutical agent diltiazem illustrated in this example.

This example will also serve to prove the in vivo functionality of the system of the invention.

Tablets of the following structure were prepared:

| Shell Composition | |
|---|---|
| Cellulose-2,5-acetate | 225 parts by weight |
| Polyethylene Glycol 600 | 112.5 parts by weight |
| Core Composition | |
| Diltiazem Hydrochloride | 180.0 mg |
| PVA 55/12 | 78.8 mg |
| Potassium Sulphate | 250.2 mg |
| Magnesium Stearate | 1.0 mg |
| Total Weight | 510.0 mg |

The core composition is compressed according to conventional procedures into formed bodies having a diameter of 9 mm. The shell composition is placed in an acetone solution and applied to the core to form a shell thickness of 30 $\mu$m using conventional methods. The shell which is produced is a permeable shell, that is, it is permeable to the passage of active agent.

In an open, randomized, double cross-over study, the pharmacokinetic parameters which occurred after the administration of one diltiazem retard formulation containing 90 mg and one containing 180 mg of active agent were examined:

a) Reference Drug/"Treatment U": 90 mg of a retard tablet (commercial drug) Amount of active agent 90 mg of diltiazem b) Test Drug/"Treatment K": Diltiazem retard 180 mg, tablets of the invention according to Example 2, amount of active agent 180 mg of diltiazem The quantitative determination of diltiazem and its major metabolite desacetyl diltiazem was carried out in a plasma using a specific, validated HPLC method. The lowest quantification level was 2 ng diltiazem/ml of plasma and 1 ng of desacetyl diltiazem/ml of plasma. The study included four male volunteers aged between 18 and 40, all of whom completed the study according to instructions.

The test persons appeared on the different occasions as determined by the randomization plan, separated by wash-out phases of one week, to receive administrations of diltiazem. Food intake was inhibited for ten hours before and up to four hours after each drug administration.

Immediately prior to drug administration (predose) and after 1, 2, 3, 4, 6, 8, 10, 12, 24, 30, 36 and 48 hours, 10 ml venous blood samples were taken and plasma obtained to determine the concentration of diltiazem and desacetyl diltiazem.

FIG. 1 illustrates the in vitro release pattern of diltiazem as the mean value of six determinations of tablets prepared according to Example 2. A lag phase in which active agent release is lower can be seen in FIG. 1.

Figure 2:
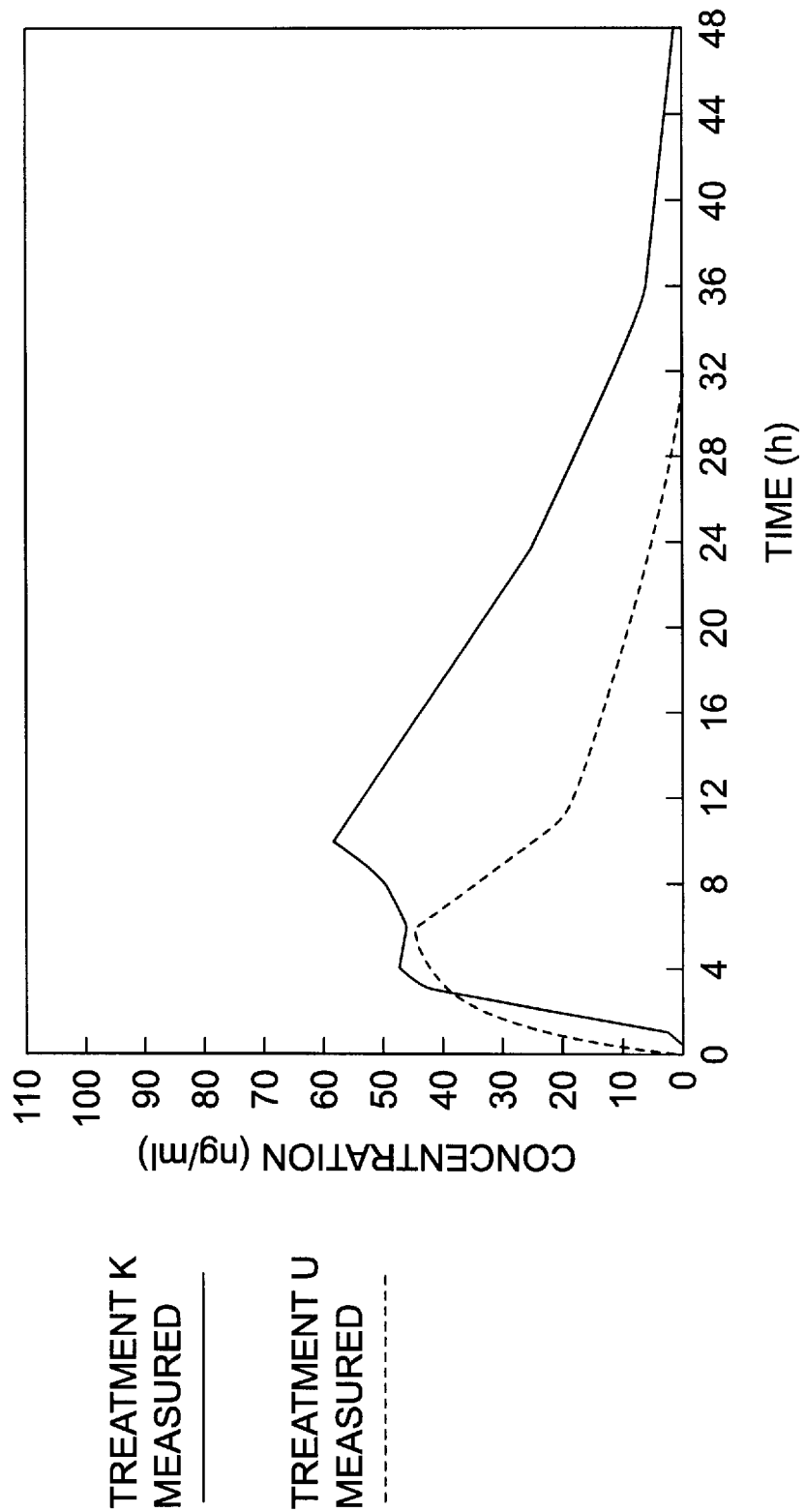
FIG. 2 shows the plasma level following the administration of the diltiazem pharmaceutical preparation according to Example 2 ("Treatment K") in comparison to a commercial retard drug ("Treatment U")
Figure 3:
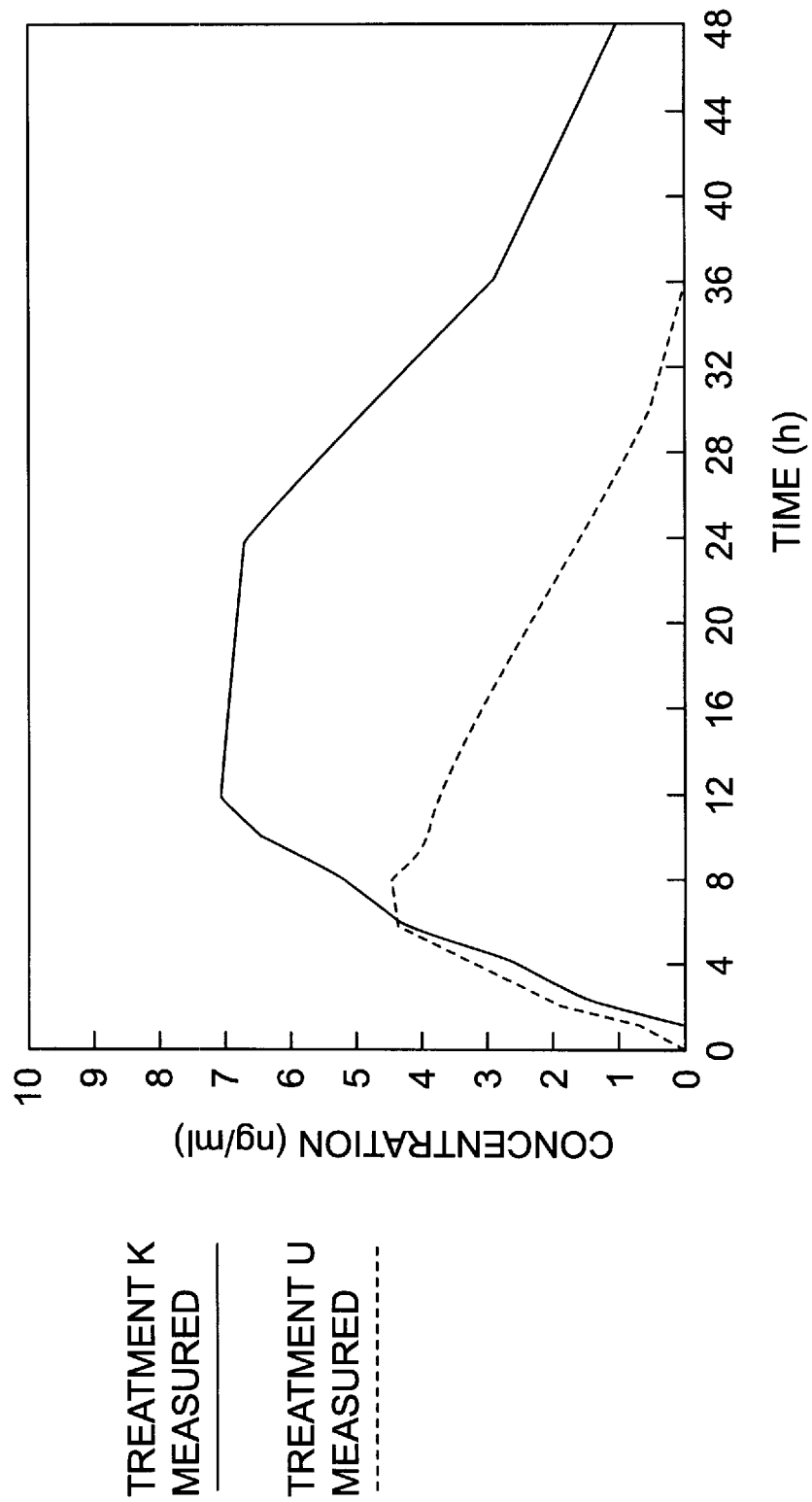
FIG. 3 shows the plasma level of the major metabolite desacetyl diltiazem following the administration of the diltiazem pharmaceutical preparation according to Example 2 ("Treatment K") in comparison to a commercial retard drug ("Treatment U").

The plasma levels of diltiazem as mean values calculated for groups of four volunteers each, following the single administration of the two preparations, are shown in FIG. 2, which shows the clear advantage of the system according to the invention in view of both the availability and the duration of the minimal therapeutic concentrations, despite the higher dosage according to Example 2. The pharmaceutical preparation according to Example 2 enables single daily doses.

These results prove the plausibility of the analysis method and underline the significance of the results.

It will be understood that the above description of the present invention is susceptible to various modifications, changes and adaptations, and the same are intended to be comprehended within the meaning and range of equivalents of the appended claims.

What is claimed is:

1. A system for the controlled release of an active agent to an environment of use, said system having a predetermined zero-order release rate of the active agent to the environment of use, comprising:

a) a shell formed of a water-insoluble material which is permeable to the passage of an external fluid, b) a core which is surrounded by said shell, and comprised of i) a water-soluble active agent, and ii) a water-soluble polyvinyl alcohol polymeric adjuvant having a lesser ability to become solved in water than the active agent, said active agent and said polymeric adjuvant being hydrated when the external fluid permeates through the shell, said active agent being present in an amount which provides a saturated solution of active agent in the core at said predetermined zero-order release rate to thereby provide a predetermined solved amount of said active agent at said predetermined zero-order release rate, said polymeric adjuvant being a polymer which precipitates in a saturated aqueous solution of the active agent and being present in an amount which provides a saturated solution of said polymeric adjuvant at said predetermined zero-order release rate to thereby provide a predetermined solved amount of polymeric adjuvant at said predetermined zero-order release rate, and said predetermined solved amounts of active agent and polymeric adjuvant creating a predetermined hydrostatic pressure, iii) wherein the active agent and polymeric adjuvant are present in a ratio such that iv) if the release rate of the active agent deviates from the predetermined zero-order release rate by being higher than the predetermined zero-order release rate, an additional amount of polymeric adjuvant becomes solved and is delivered to the shell where it acts to decrease the permeability of the shell and thereby decrease the deviation and V) if the release rate of the active agent deviates from the predetermined zero-order release rate by being lower than the predetermined zero-order release rate, an additional amount of active agent becomes solved to increase the hydrostatic pressure above said predetermined hydrostatic pressure, said increased hydrostatic pressure acting on said shell to increase the permeability of the shell and thereby decrease the deviation.

2. The system according to claim 1, wherein the shell is comprised of a material which is substantially impermeable to the passage of the active agent, and is provided with a passageway for dispensing said agent from the system.

3. The system according to claim 1, wherein the shell is comprised of a material which is permeable to the passage of the active agent.

4. The system according to claim 1, wherein the shell is comprised of a material which is substantially impermeable to the passage of the active agent, and is not provided with any pas- sageway through the shell.

5. The system according to claim 1, wherein the active agent is a pharmaceutical agent for use in human or veterinary medicine.

6. The system according to claim 1, wherein the active agent is a plant protective, a fertilizer or a growth regulator.

7. The system according to claim 1, wherein the shell is semipermeable and has at least one release opening for the active agent.

8. The system according to claim 1, wherein an osmotically active adjuvant is present in the core in admixture with the active agent.

9. The system according to claim 8, wherein the osmotically active adjuvant is a substance with buffer activity.

10. The system according to claim 8, wherein the osmotically active adjuvant is selected from lactose, fructose, dextrose, sucrose, mannitol, sodium chloride, potassium chloride, potassium sulphate, mono- di- and trisodium phosphate, or mixtures thereof.

11. The system according to claim 8, wherein the admixture of osmotically active adjuvant and active agent is present in an amount of 2 to 98 weight percent, based on the total weight of the core.

12. The system according to claim 1, wherein the polyvinyl alcohol has a polyvinyl acetate content of 6 to 18 weight percent and an molar mass of 20,000 to 70,000.

13. The system according to claim 1, wherein the polymeric adjuvant capable of unlimited swelling is present in an amount of 2 to 90 weight percent, based on the total weight of the core.

14. The system according to claim 1, wherein the film former for the shell is cellulose acetate, ethyl cellulose, polyvinyl acetate or a polyacrylic acid copolymer.

15. The system according to claim 1, wherein the shell contains a plasticizer.

16. The system according to claim 15, wherein the plasticizer is a polyethylene glycol which has an average molecular weight of 400 to 20,000, and is present in an amount of 2 to 30 weight percent, based on the weight of the film former.

17. The system according to claim 1, wherein the system is present, at least partially, in a multi-compartment form.

18. The system according to claim 1, wherein the system is present as a microform.

19. The system according to claim 1, wherein the active agent is present in an amount of 2 to 98 weight percent, based on the weight of the core.

20. A process for the preparation of a system for the controlled zero-order release of an active agent comprising, mixing at least one water-soluble active agent with at least one osmotically active adjuvant and at least one water-soluble Polyvinyl alcohol polymeric adjuvant having a lesser ability to become solved in water than the active agent and osmotically active adjuvant and which precipitates in a saturated aqueous solution of the active agent and osmotically active adjuvant, compressing the mixture into a core, and then covering the core with a shell made of a film former and a soluble, hydrophilic or hydrophobic plasticizer.

* * * * *